(12) United States Patent  
Zelechonok (10) Patent No.: US 10,012,620 B1
(45) Date of Patent: Jul. 3, 2018

(54) CHROMATOGRAPHY SAMPLE INTRODUCTION DEVICE

(71) Applicant: Yury Zelechonok, Northbrook, IL (US)

(72) Inventor: Yury Zelechonok, Northbrook, IL (US)

(73) Assignee: SIELC Technologies Corporation, Wheeling, IL (US)

( * ) Notice: Subject to any disclaimer, the term of this patent is extended or adjusted under 35 U.S.C. 154(b) by 106 days.

(21) Appl. No.: 15/089,461

(22) Filed: Apr. 1, 2016

Related U.S. Application Data (60) Provisional application No. 62/144,170, filed on Apr. 7, 2015.

(51) Int. Cl.
| | |
|---|---|
| *G01N 30/16* | (2006.01) |
| *G01N 30/18* | (2006.01) |
| *G01N 1/14* | (2006.01) |
| *B01D 15/12* | (2006.01) |
| *G01N 30/22* | (2006.01) |
| *B01D 15/14* | (2006.01) |
| *G01N 1/10* | (2006.01) |

(52) U.S. Cl.
CPC ............ *G01N 30/18* (2013.01); *B01D 15/125* (2013.01); *B01D 15/14* (2013.01); *G01N 1/14* (2013.01); *G01N 30/22* (2013.01); *G01N 2001/1056* (2013.01); *G01N 2030/185* (2013.01)

(58) Field of Classification Search
CPC .. G01N 30/18; G01N 2030/185; G01N 30/16; G01N 30/22; G01N 2001/002; G01N 2001/1056; G01N 35/10; G01N 35/1009; G01N 2035/1053; B01D 15/12; B01D 15/125; B01D 15/14; B01L 3/5023; B01L 3/508

See application file for complete search history.

(56) References Cited

U.S. PATENT DOCUMENTS

| | | | |
|---|---|---|---|
| 4,182,184 A | 1/1980 | Bakalyar et al. | |
| 5,858,000 A * | 1/1999 | Novacek | A61L 2/28 604/110 |
| 5,861,317 A | 1/1999 | Tanihata | |
| 6,290,909 B1 | 9/2001 | Paul et al. | |
| 7,776,615 B2 * | 8/2010 | Yuka | B01D 15/00 422/261 |
| 8,173,070 B2 | 5/2012 | Gerhardt et al. | |
| 8,544,350 B2 | 10/2013 | Itafuji et al. | |
| 8,574,918 B2 | 11/2013 | Hirayama et al. | |

(Continued)

*Primary Examiner* — Justin Olamit
(74) *Attorney, Agent, or Firm* — John C. Shepard (57) ABSTRACT

A disposable chromatography sample introduction device includes a stylus with a holder and a tubular stem extending from one end of the holder containing porous sample-holding material. The stylus has a pair of spaced openings permitting fluid flow therethrough. An injector housing includes an insertion port for receiving the stylus, a seal, an inlet port for communicating with one stylus opening, and an outlet port for communicating with the other stylus opening. When the stem is immersed in a sample, sample enters the stem by capillary action. Thereafter, the stylus is inserted into the housing insertion port where mobile phase flowing from inlet port to outlet port passes through the stem extracting sample. The holder has a finger grip and an external thread that engages a complementary injector housing thread to secure the holder when the stylus is inserted therein.

23 Claims, 9 Drawing Sheets

(56) References Cited

U.S. PATENT DOCUMENTS

2007/0113616 A1* 5/2007 Schilling ............... G01N 30/18
                                                    73/23.41
2012/0160038 A1* 6/2012 Wells ..................... B01J 15/00
                                                    73/863.21

* cited by examiner

CHROMATOGRAPHY SAMPLE INTRODUCTION DEVICE

CROSS-REFERENCE TO RELATED APPLICATIONS

This application claims the benefit of Provisional Patent Application Ser. No. 62/144,170, filed Apr. 7, 2015.

BACKGROUND OF THE INVENTION

Technical Field

The present invention relates to chromatography sample introduction and, more particularly, to a simple device that can be used to collect a liquid sample and introduce it into a chromatography system for analysis.

Background Art

High pressure liquid chromatography (HPLC) system usually includes a high pressure pump, an autosampler or some other sample introduction device, a chromatography column, and a detector.

The sample typically is a solution of analytes in an appropriate solvent. The required portion of the sample is injected into the chromatography liquid stream generated by the high pressure pump and is separated to individual components in the column. The separated components of the sample are measured individually by the detector.

The column separation media or stationary phase is made of fine bits of solid material usually silica gel having a size of 5 micrometers or smaller. These bits are encapsulated in a tube with a filter at each end that keeps the bits layer undisturbed at high pressure while allowing liquid of the mobile phase to flow through the bits layer.

Due to the small size of the bits and the fine pores of the two filters, the liquid stream passing through the column should be essentially free of solid contaminants. While the mobile phase is generally free of solids, the samples usually are not. Great care needs to be taken to eliminate all the possible non-soluble components or particulates of the sample that might enter the flow. Otherwise, the particulates will settle on the column filter or on the column layer itself and essentially block the column flow after several injections.

If contamination free sample introduction is hard to achieve, various in-line devices or components are typically are added to the system. One such component is an in-line filter that can be easily replaced or cleaned after several injections. Another such component is a guard column, which is essentially a small column connected serially upstream of the main separation column that can be easily replaced when it becomes plugged with insoluble matter. The guard column is smaller than the main column and is less expensive.

To eliminate contamination by sample matter, different cleaning techniques are used. Sample filtering before injection is one such process. However, this requires much more sample than is actually required for analysis.

Another cleaning technique is centrifuge cleaning. This also requires extra sample and takes time and additional equipment.

Still another technique is to use a solvent replacement to coagulate unwanted components, such as proteins and polymers, by changing the solvent composition of the sample followed by filtration or centrifugation.

Yet another cleaning technique is solid phase extraction (SPE). The SPE device is a cartridge filled with appropriate solid adsorbent. The liquid analytes solution, when it is pushed through the SPE cartridge, becomes entrapped on the solid adsorbent contained in the cartridge. All the other components of the sample stay in solution. Thereafter, the analytes are recovered from the cartridge by using another solvent.

There are many other techniques that are employed to clean samples in preparation for chromatographic analysis, but all cleaning techniques are time consuming, require excess sample, or use some additional disposable components or additional equipment. In addition, they are prone to have a negative effect on the accuracy of sample's quantitative results, especially in trace analysis, since every additional step in sample manipulation causes some irreversible analyte loss.

An additional problem is that the sample in all these cleaning processes require that the holding container be changed several times and this complicates tracking of the original sample to the analysis result.

A further problem associated with the use of different sample cleaning equipment is the potential cross-contamination of the samples. It is a significant problem, especially in a regulated environment.

BRIEF SUMMARY OF THE INVENTION

The present invention is directed to overcoming one or more of the problems as set forth above.

The primary object of the present invention is to provide a device that allows simple introduction of a sample into the chromatography system.

It is a further object of the present invention to provide a device that is inexpensive and can be disposed of after a single use.

It is also an object of the invention to provide a device that eliminates sample loss.

It is an additional object of the present invention to provide a device that eliminates sample cleaning.

It is another object of the present invention to provide a sample introduction device that can be used without any additional equipment.

It is another object of the present invention to provide a sample introduction device that requires very small sample amounts and that can be used for all analysis without any loss.

It is another object of the present invention to provide a sample introduction device which can hold the sample from the time of sample collection all the way to the time of the testing without changing the holding container, thereby offering a simple and reliable sample tracking method.

It is still another object of the present invention to provide a sample introduction device that is essentially free of cross-contamination between samples.

It is still another object of the present invention to provide a injector stylus that is suitable for both small and big sample volumes.

In an exemplary embodiment of the present invention, an injector stylus includes a tubular stem filled with porous dry solid material and a holder at one end. The stylus has an inlet opening and an outlet. An injector housing is provided that has an injection port adapted to securely receive the stylus and has a high pressure inlet port communicating with the inlet opening and a high pressure outlet port communicating with the outlet opening.

The stem can be immersed in sample solution so that sample liquid fills the porous material by capillary action with the outlet opening acting as a vent to ambient atmosphere.

In an embodiment of the invention, the holder has a threaded portion that engages a complementary threaded port in the injector housing to allow the stem to be tightly held and form a sealed mobile phase passage from the inlet to the outlet.

In an embodiment of the invention, a seal is provided between the housing and the stem intermediate the two stylus openings to prevent leakage of liquid at high pressure.

In a preferred embodiment of the invention, the injector stylus may include a metal or plastic disk to write on or a tag providing electronic storage of sample information.

BRIEF DESCRIPTION OF THE SEVERAL VIEWS OF THE DRAWINGS

The details of construction and operation of the invention are more fully described with reference to the accompanying drawings which form a part hereof and in which like reference numerals refer to like parts throughout.

In the drawings:

FIG. 9 is a perspective view of the injector stylus shown in FIG. 2 with a cover screwed on;

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood.

DETAILED DESCRIPTION OF THE PREFERRED EMBODIMENTS

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

This invention generally relates to high pressure liquid chromatography ("HPLC") and to ultra high pressure liquid chromatography ("UHPLC"), but is not limited thereto and may by employed in other fields as well.

Figure 1:
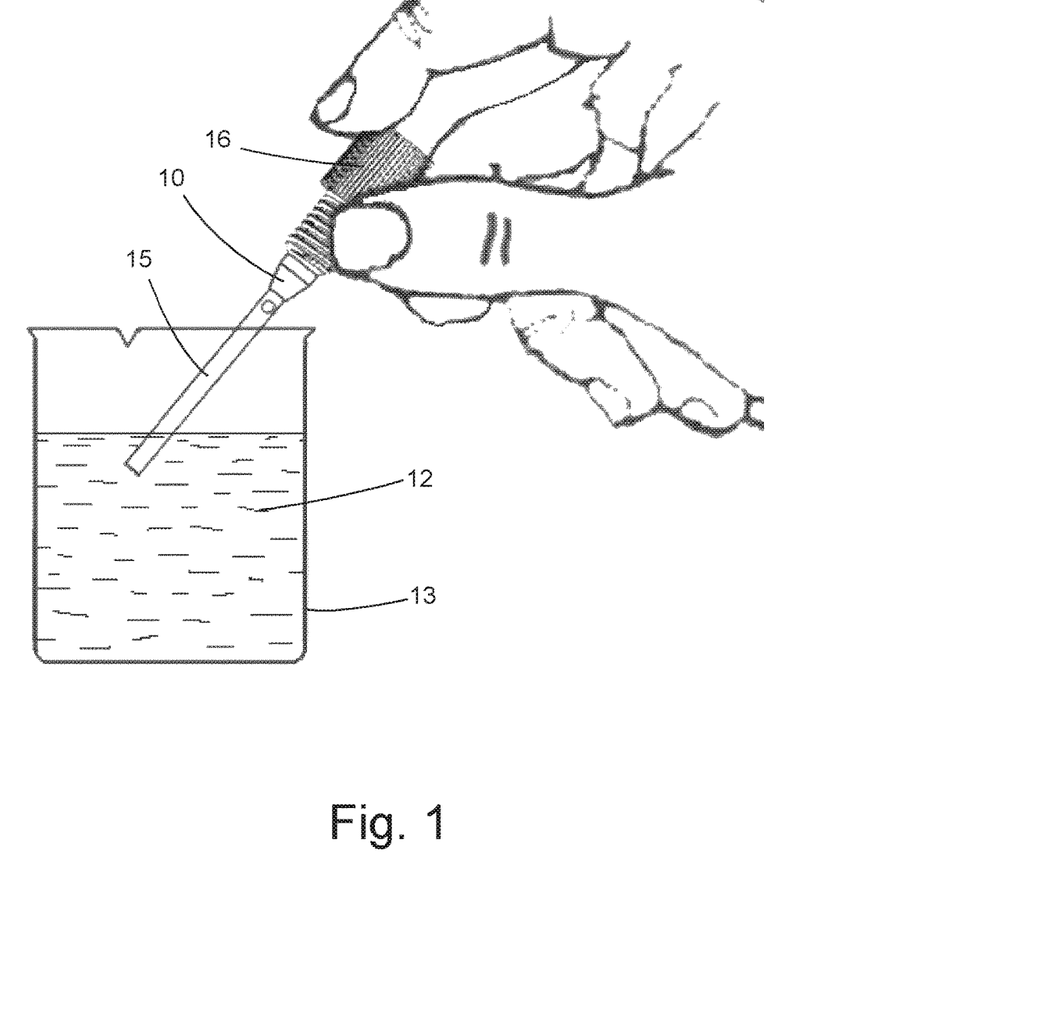
FIG. 1 is a view of an injector stylus employing the principles of the invention being used to obtain a sample.

As seen in FIG. 1, a sample introduction device, generally designated 10, is being used to withdraw a sample from a solution 12 contained in a beaker 13.

In FIGS. 2-8, a first exemplary embodiment of the sample introduction device, or injector stylus 10, is seen to broadly include a rigid hollow stem 15 and a holder 16. The stem 15 is an elongate thin-walled tube 18 extending axially along a longitudinal axis and having a proximal end 20 fixed to the holder 16 and a distal free end 21. The straight tube 18 has a cylindrical side wall defining a flow passage 23 therethrough and an outer surface which has a circular cross-section of constant external diameter for the length thereof. The tube 18 can be made of rigid material, such as metal, glass or plastic.

The tube 18 has an axial opening 25 at its distal end 21 and a pair of radial openings 26 extending through the side wall of the stem 15. The radial openings 26 are formed inboard of the distal end 28 of the holder 16 and extend laterally through the tube wall 27. As will be seen later, there may be any number of outlet openings spaced circumferentially around the tube 18 ensuring that fluid communication is enabled laterally outward from the tube flow passage 23.

The hollow tube 18 is filled entirely with solid dry porous absorbing material 31. The porous material 31 is permeable and is comprised of porous plastic, porous sintered metal, cellulose fibers, silica gel rod, or other similar or suitable materials, and should have an open pore structure. Because of the porous nature of this material, the injector stylus 10 can absorb a sample solution when immersed in a liquid as shown in FIG. 1.

Figure 9:
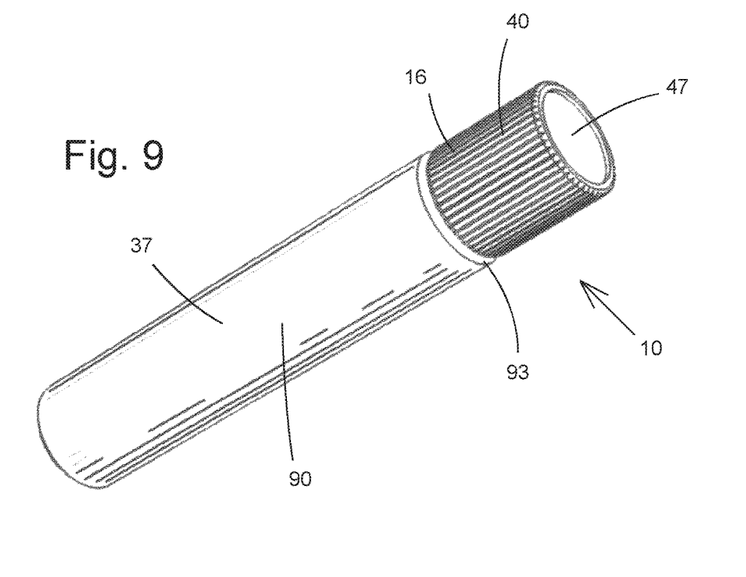
Figure 10:
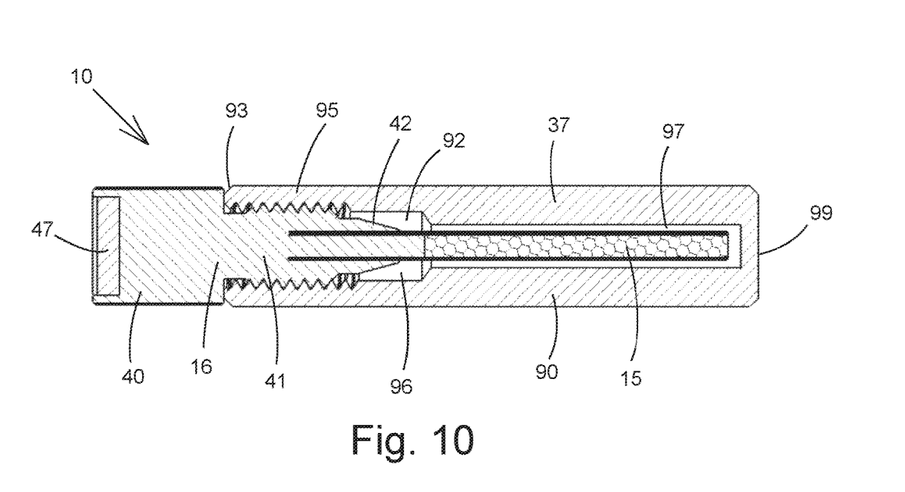
FIG. 10 is a cross-sectional view of the injector stylus and cover shown in FIG. 9.

Given that the tube volume and the free space inside of the filled tube 18 is fixed, the amount of absorbed solution is constant among identically made sample introduction devices. Absorbed sample liquid can be stored inside the injector stylus 10 until it is used for analysis. To eliminate evaporation and spoilage of the sample, an appropriately sized cover 37 as shown in FIGS. 9 and 10 or a plastic bag (not shown) can be provided.

Figure 4:
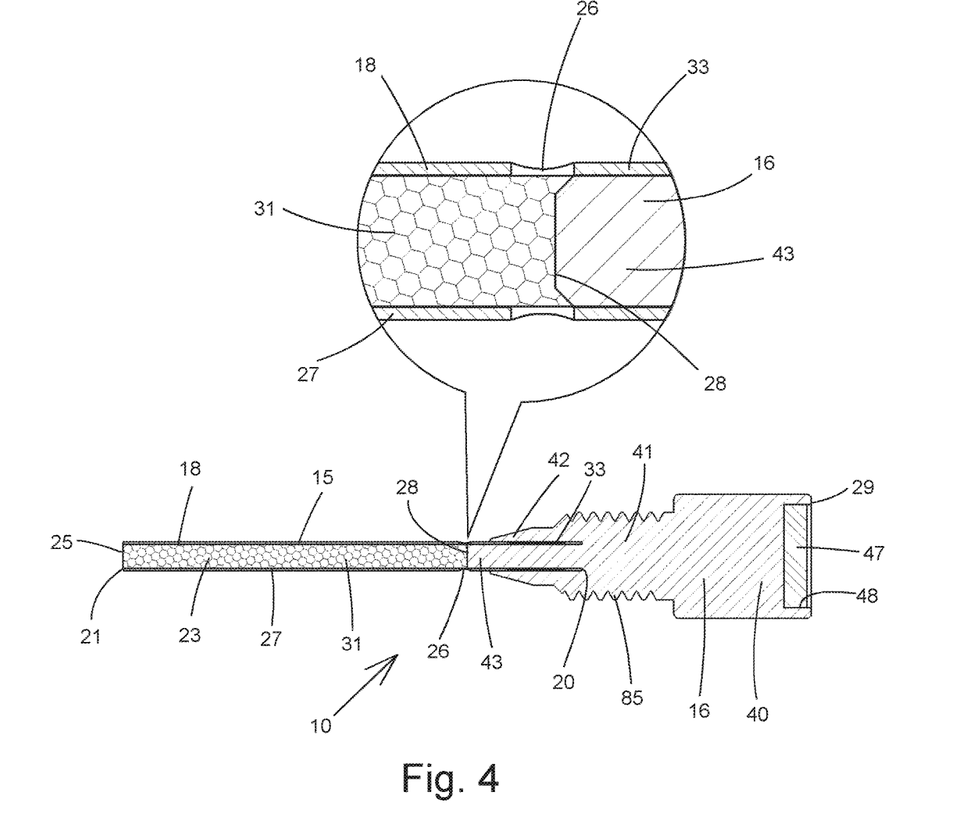
FIG. 4 is a cross-sectional view and a partial enlargement of the injector stylus shown in FIG. 2.
Figure 5:
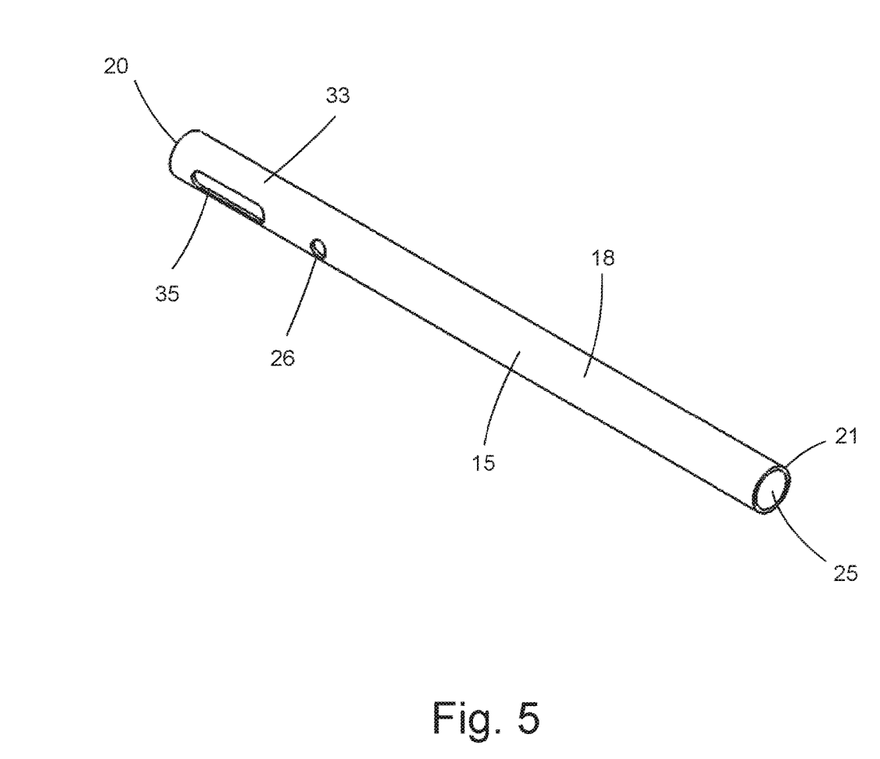
FIG. 5 is a perspective view of a tubular stem forming a part of the injector stylus shown in FIG. 2

To mount the sampler stem 15 and close the proximal end of the flow passage 23, the proximal end portion 33 of the rigid tube 18 is embedded in or otherwise firmly connected to the holder 16, which may be formed from plastic or other suitable material. To facilitate gripping, the holder 16 is diametrically larger than the stem 15. The proximal end portion 33 of the tube 18 is formed with one or more elongate slots 35 extending transversely across the tube 18 so that during manufacture the holder material extends through the tube interior to positively hold the tube 18 firmly therewithin.

The holder 16 generally includes a proximal, externally-fluted finger-grippable end portion 40, an externally-threaded intermediate portion 41, an intermediate frusto-conical tapered portion 42, and a distal mounting portion 43 that plugs the proximal end of the tube 18. The mounting portion 43 extends into the tube proximal end portion 33 and terminates adjacent the radial openings 26 thereby blocking fluid flow through the tube passage 23 beyond the outlet openings 26 and minimizing dead space.

Figure 2:
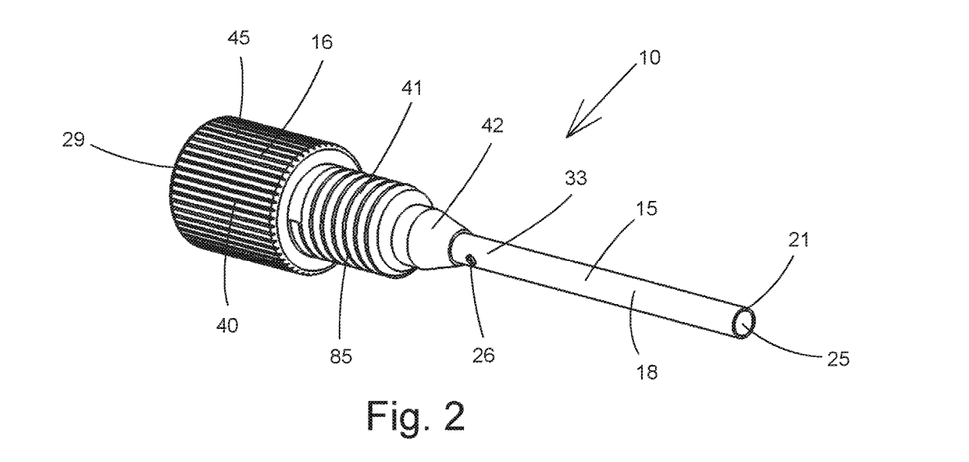
FIG. 2 is an external perspective view of an embodiment of an injector stylus employing the principles of the invention.
Figure 3:
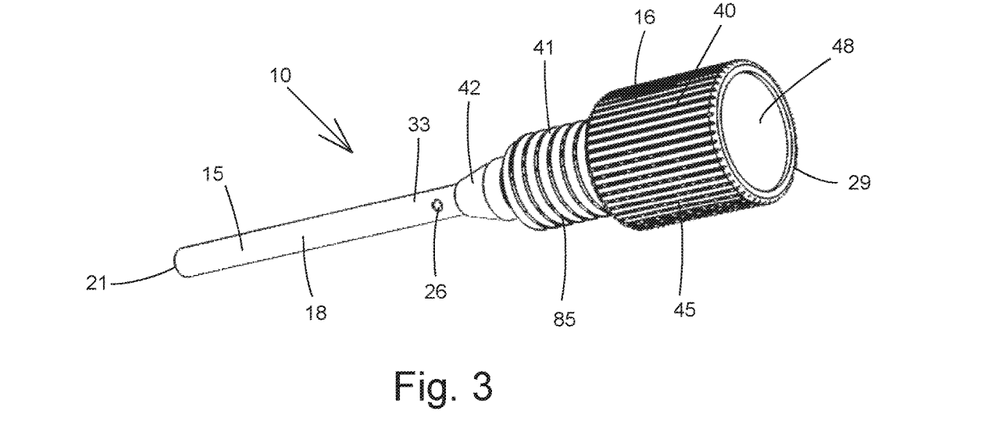
FIG. 3 is an external perspective view of the injector stylus shown in FIG. 2 from a different viewpoint.

The grooves and ridges 45 on the exterior of the holder 16 allow a user to conveniently grip and manipulate the stem 16 when sampling and to introduce the stem 16 into the chromatography system for analysis. The injector stylus 10 can have a metal or plastic component 47 inserted in an opening 48 defined in the proximal end 29 of the grip portion 40 to provide space for information write up or for insertion of a unique electronic tag.

Figure 6:
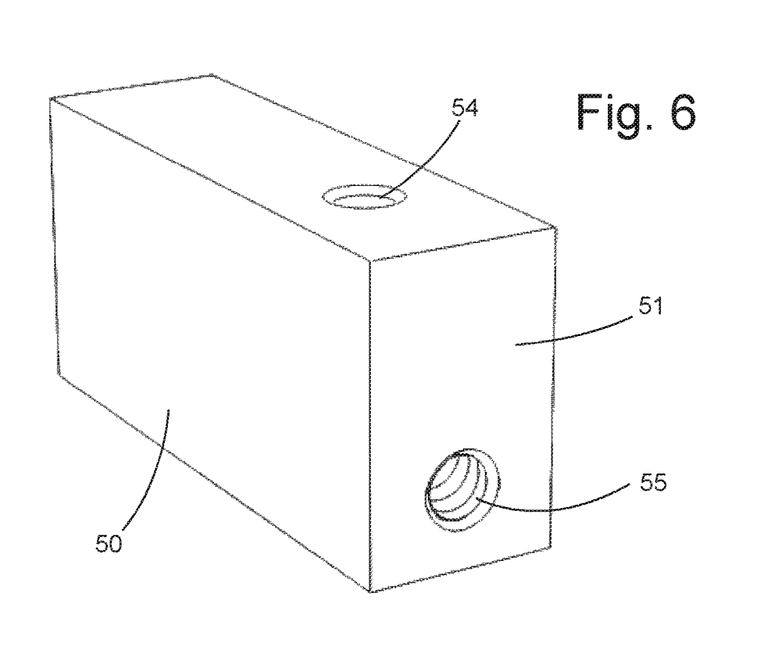
FIG. 6 is an external perspective view of an injector compatible with the injector stylus shown in FIG. 2; and, FIG. 7 is a cross-sectional view of the injector shown in FIG. 6.
Figure 7:
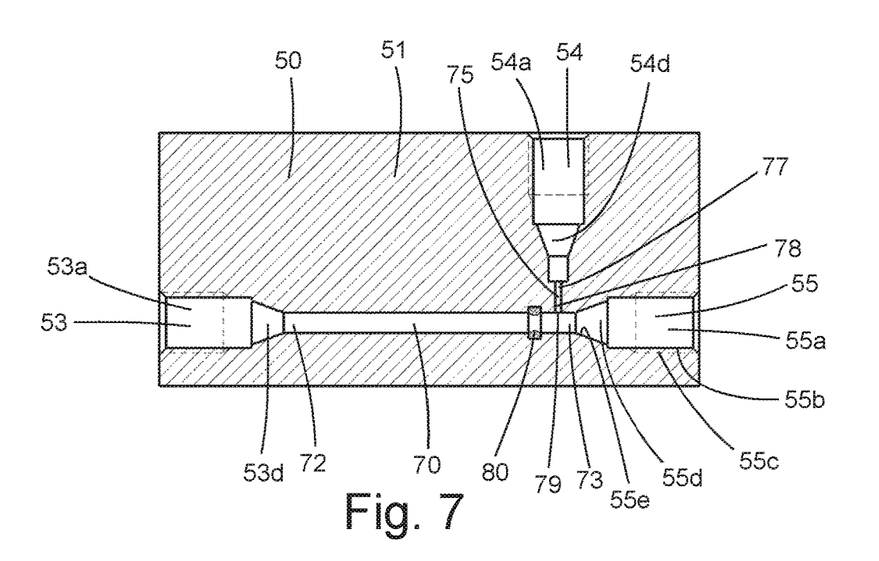

To enable introduction of collected sample into a chromatography system, an injector 50 is provided. The injector 50 has a housing 51 that includes a fluid port 53, a fluid port 54, and an insertion port 55 for receiving the injector stylus 10. Herein, it is understood that port 53 is an inlet and port 54 is an outlet with port 53 being downstream from the high pressure pump (not shown) and the port 54 being upstream of the chromatography column and detector (not shown).

The insertion port 55 is configured and sized to receive the injector stylus 10. Similarly, the inlet and outlet ports 53 and 54 are each configured and sized to receive conventional chromatography connectors and couplings. Each port 53,54, 55, respectively, includes a circular bore 53a,54a,55a having a large outer portion 53b,54b,55b with an internal female thread 53c,54c,55c extending longitudinally inward of the housing outer surface, and an intermediate unthreaded portion 53d,54d,55d with a frusto-conical internal surface 53e, 54e,55e. The ports 53,54,55 are in fluid communication with interconnected sections of the internal flow passages.

A first flow passage section 70 of circular cross-section extends axially between a first end 72 at the inlet port 53 and a second end 73 at the insertion port 55. The flow passage section 70 is sized and configured to receive the stem 15, the internal diameter of the flow passage section 70 and the external diameter of the stem 15 being similar such that the stem 15 slides smoothly into the flow passage section 70. The external diameter of the stem wall is substantially the same as or less than the internal diameter of said housing flow passage into which it is inserted. Fluid flowing downstream from the pump enters the inlet port 53 and flows through the tube 18 from its open upstream end 21 toward its downstream end 20.

A second flow passage section 75 extends between a first end 77 at the outlet port 54 and a second end 78 where it intersects the first flow passage section 70. The second flow passage section 75 is disposed so that it is transverse to and communicates with the first flow passage section 70 at intersection 79 where the radial openings 26 of the stem 15 are positioned when the injector stylus 10 is fully inserted into the insertion port 55. As a result, fluid flow from the tube passage 23 will exit laterally from the stem 15 into the second flow passage section 75 and travel from the outlet port 54 to the downstream column (not shown).

A resilient annular seal or O-ring 80 is disposed along the first flow passage section 70 in an annular internal groove (not numbered) upstream of the second flow stream intersection 79 to provide a seal between the housing 51 and the stem 15 and prevent the flow of fluid externally past the stem 15.

Figure 8:
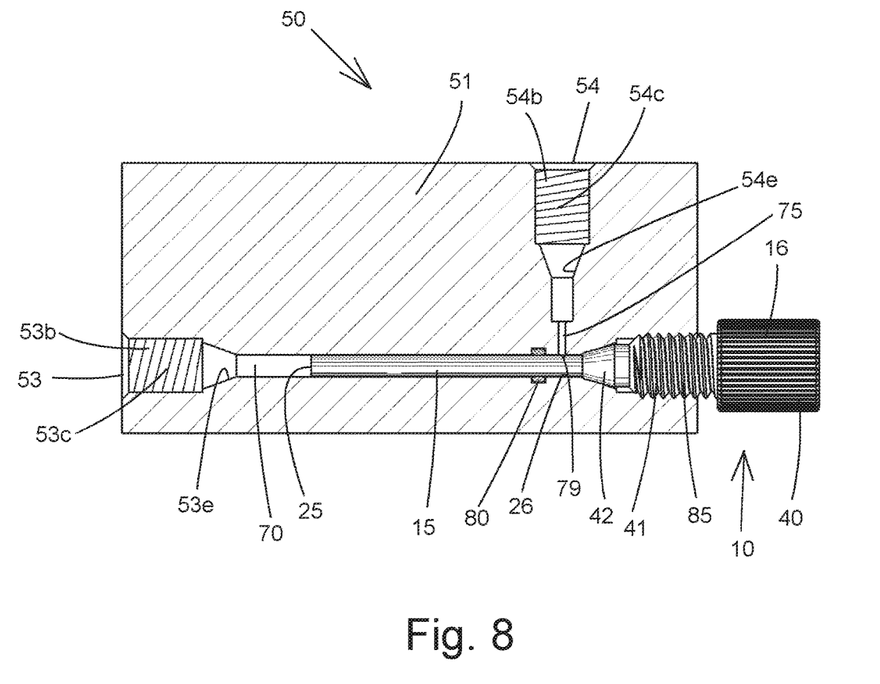
FIG. 8 is a cross-sectional view of the injector shown in FIG. 6 with an injector stylus inserted therein.

During use, the stem 15 is inserted into the insertion port 55 with its external male threads 85 engaging the insertion port internal female threads 55c upon manual rotation of the grip to secure the stem 15 within the first flow passage 70. When fully inserted, the tube axial opening 25 communicates with the port flow passage 70 and the tube radial openings 26 are axially aligned with the port flow passage 75 to communicate therewith. The injector stylus 10 forms a high pressure sealed flow path through porous material effectively filtering all potential solid contaminations and provides for the transfer of the sample from the sample introduction device to the downstream separation column when solvent is passed through the stem 15 to wash sample from the porous material 31.

Referring to FIGS. 9 and 10, the injector stylus 10 is shown screwed onto the cover 37. The cover 37 is a cylinder 90 having an external surface diameter similar to the external diameter of the grippable portion 40 of the holder 16 and has a longitudinal internal opening 92 extending axially from a proximal end 93. The opening 92 includes an outer internally threaded portion 95 for cooperation with the threads of the holder 16 intermediate portion 41, a intermediate narrowing cavity 96 circumscribing the holder tapered portion 42, and a elongate inner bore 97 surrounding the stylus stem 15 and terminating inward of the endwall at the distal end 99 of the cover 37. The inner bore 99 has an internal diameter greater than the external diameter of the stem 15. The length of the opening 92 allows an inserted stem 15 to be releasably held by and completely sealed within the cover 37.

Figure 11:
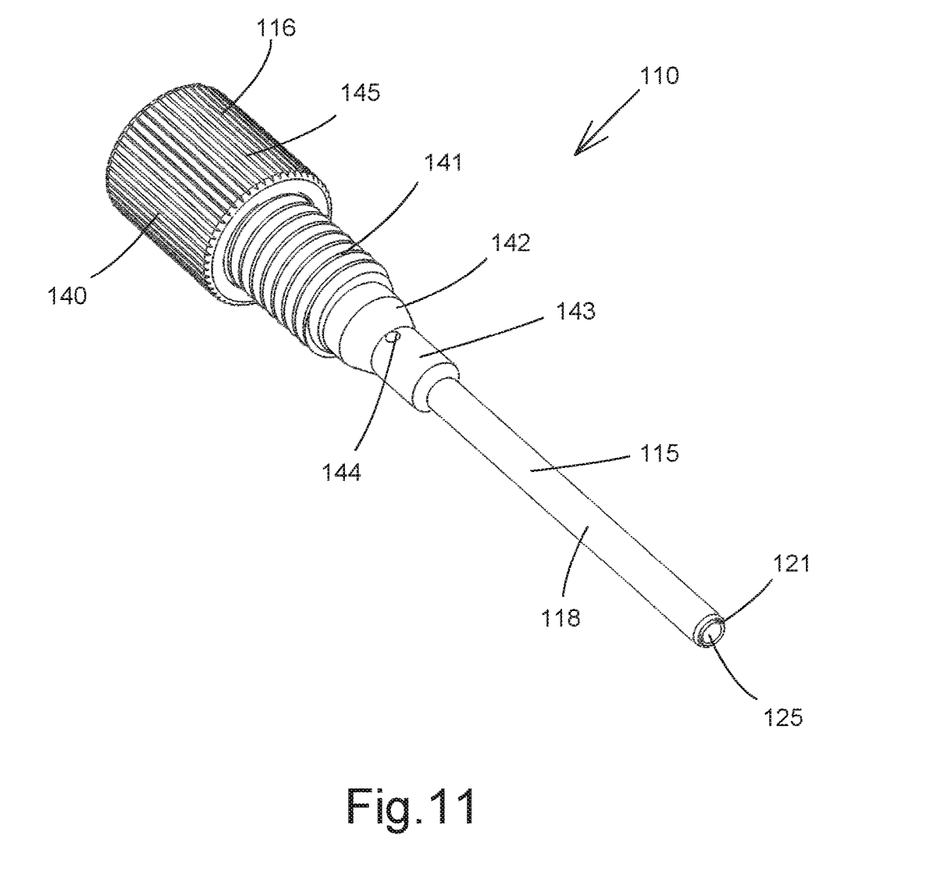
FIG. 11 is a perspective view of a second embodiment of the injector stylus.
Figure 12:
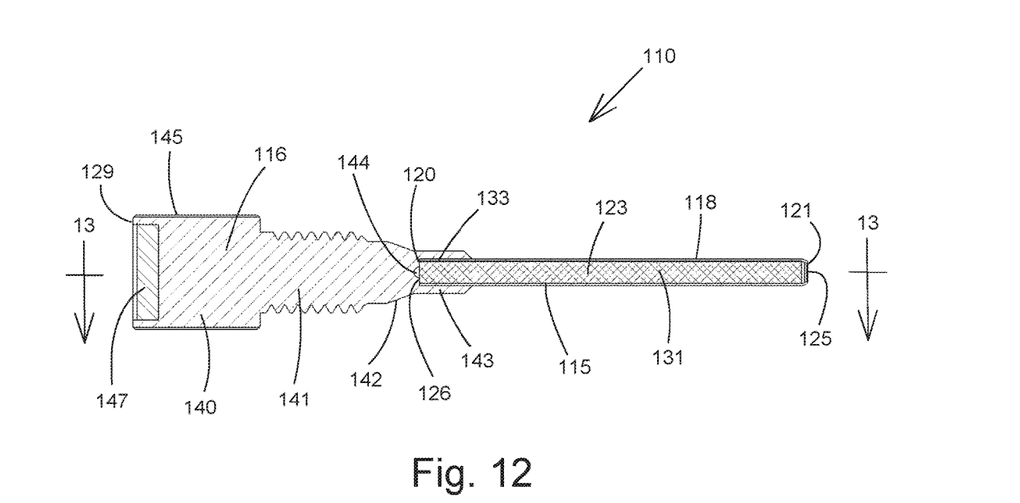
FIG. 12 is a cross-sectional view of the injector stylus shown in FIG. 11.
Figure 13:
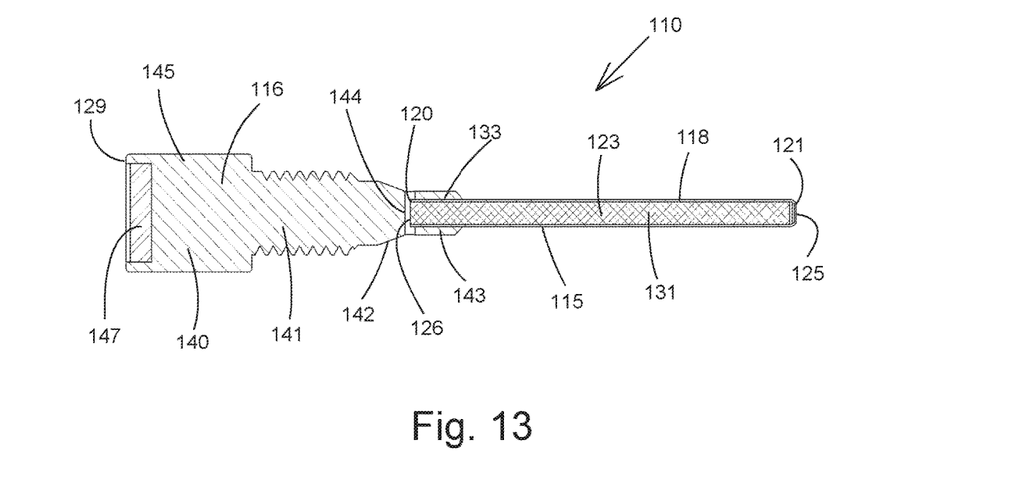
FIG. 13 is a cross-sectional view of the injector stylus shown in FIG. 12 taken along line 13-13.

In FIGS. 11-13, a second embodiment of the sample introduction device, or injector stylus 110, is seen and is constructed and functions similarly to the first embodiment described above. The injector stylus 110 broadly includes a rigid hollow stem 115 and a holder 116. The stem 115 is an elongate thin-walled tube 118 extending axially along a longitudinal axis and having a proximal end 120 fixed to the holder 116 and a distal free end 121. The straight tube 118 has a cylindrical side wall defining an internal flow passage 123 therethrough and an outer surface which has a circular cross-section of constant external diameter for the length thereof. The tube 118 has an axial opening 125 at its distal end 121 and an axial opening 126 at its proximal end 120. Like the first embodiment, the hollow tube 118 is filled with solid dry porous absorbing material 131 that will hold sample until the tube is washed by fluid flowing through the tube 118 to extract the sample.

To mount the stem 115, the proximal end portion 133 of the rigid tube 118 is embedded in or otherwise firmly connected to the holder 116. To facilitate gripping, the holder 116 is diametrically larger than the stem 115. The holder 116 generally includes a proximal, externally-fluted finger-grippable end portion 140, an externally-threaded intermediate portion 141, a frusto-conical tapered portion 142, and a generally cylindrical distal mounting portion 143.

The proximal end 120 of the stem 115 is fixed in the holder 116 and terminates at a position approximately between the tapered portion 142 and mounting portion 143. A transverse passageway 144 extends through the mounting portion 143 intersecting the proximal end 120 of the stem 115 and is in fluid communication with the stem internal flow passage 123.

When the injector stylus 110 is inserted into the injector 50 and the complementary external threads on the holder 116 and the internal threads of the housing insertion port 55 are joined together, the stylus 110 is secured to the injector housing 51 and the stem 115 is sealed therewithin. Fluid can then be delivered upstream into the stem distal end opening 125, passed through the stem internal flow passage 123 containing the sample-holding media 131 and the stem proximal end opening 126, and withdrawn downstream via the transverse passageway 144.

While it is preferred that the stem axial openings are at the extreme ends of the tube 118 so that fluid flow washes the entire tube interior of sample, it is understood that the tube openings can be formed adjacent the stem ends if required. It should also be understood that the passageway 144 need not extend entirely through the holder 116, but need only have a depth to reach and intersect the stem proximal end opening.

The grooves and ridges 145 on the exterior of the holder 116 allow a user to conveniently grip and manipulate the stem 115 when sampling and to introduce the stem 115 into the chromatography system for analysis. The injector stylus 110 can have a metal or plastic component 147 inserted in an opening 148 defined in the proximal end 129 of the grip portion 140 to provide space for information write up or for insertion of a unique electronic tag.

INDUSTRIAL APPLICABILITY

It is understood that while the sample introduction device is universal for many applications, the several modifications of this device can be made available with different internal volume allowing different sample amounts to be collected and introduced into the chromatography system.

It is also understood that the porous material inside of the rigid tube can be of different natures and can play a role in sample cleaning and entrapping not only solid particles but any molecules not desirable for particular analysis.

It is also understood that the porous material inside of the rigid tube can be pretreated with different chemicals, such as derivatization agent, to make possible a chemical conversion of analytes to a new form more appropriate for a particular chromatography.

It is also understood that the porous material inside of the rigid tube can be pretreated with an internal standard of known amount to simplify quantification and provide a chromatography reference.

It should be readily apparent that other configurations and arrangements are possible.

It is understood that while the sample introduction device described herein may replace some currently used installed components, other existing components need not be changed to accommodate its use.

It should be apparent the sample introduction device and adapter described herein is a simple, functional unit that is effective and can be inexpensively mass manufactured.

The sample introduction device described herein can be very inexpensive and can be disposed after a single use.

A sample introduction device constructed in accordance with the present invention provides simple introduction of a sample into the chromatography system.

A sample introduction device constructed in accordance with the present invention provides a device free of sample loss.

A sample introduction device constructed in accordance with the present invention provides a device that eliminates sample cleaning.

A sample introduction device constructed in accordance with the present invention provides a sample introduction device that can be used without any additional equipment.

A sample introduction device constructed in accordance with the present invention requires very small sample amounts and can use an entire sample for analysis without any loss.

A sample introduction device constructed in accordance with the present invention can hold the sample from the time of sample collection all the way to the time of the testing without changing holding containers and allows easy tracking of sample and results of analysis.

A sample introduction device constructed in accordance with the present invention provides a sample introduction device that is essentially free of cross-contamination between samples.

A sample introduction device constructed in accordance with the present invention provides a sample introduction device that is suitable for both small and big sample volumes.

Other aspects, objects and advantages of this invention can be obtained from a study of the drawings and the foregoing disclosure.

It should be understood that the terms "top," "bottom," "forward," "rearward," "first," "second," "upper," "lower," "inner," "outer," "proximal," "distal," "end," "side," "horizontal," "vertical," "height," "width," "length," and similar terms as used herein, have reference only to the structure shown in the drawings and are utilized only to facilitate describing the invention. The terms and expressions employed herein have been used as terms of description and not of limitation.

As used herein, the term "axial" when used in connection with an element described herein, refers to a direction substantially parallel to the direction of the stylus stem. The term "proximal" is intended to refer to an element normally oriented or positioned toward the holder end, while the term "distal" refers to an element that is opposite the proximal end. The term "transverse" refers to a direction other than the axial direction (e.g., orthogonal or nonorthogonal). The term "fluid" refers to both liquids and gases. The term "within" shall mean "to be partially or completely inside of".

From the foregoing, it will be observed that numerous variations and modifications may be effected without departing from the spirit and scope of the invention. It will also be observed that the various elements of the invention may be in any number of combinations, and that all of the combinations are not enumerated here. It will be understood that no limitation with respect to the specific apparatus illustrated herein is intended or should be inferred. While specific embodiments of the invention have been disclosed, one of ordinary skill in the art will recognize that one can modify the materials, dimensions and particulars of the embodiments without straying from the inventive concept.

What is claimed is:

1. An injection apparatus for use in delivering sample into a liquid chromatography system, comprising:
    an injector stylus including a holder and an elongate tubular stem, said stem including a side wall with an internal diameter and an external diameter and having a proximal end mounted to said holder and extending longitudinally from said holder to a distal free end, said stylus defining an internal flow passage passing through said stem, the internal flow passage extending between a first opening and a second opening spaced from said first opening, each of said first and second openings each providing communication between said internal flow passage and the exterior of the stylus;
    an injector having a housing defining a first fluid port, a second fluid port, an insertion port, and an injector flow passage providing communication between said ports first fluid port, said second fluid port, and said insertion port;
    securing means on said stylus and said injector for holding said stylus within said injector when said stylus is inserted through said insertion port into said injector flow passage;
    wherein said injector stylus when inserted closes said insertion port with said first opening communicating with one of said first and second fluid ports and said second opening communicating with the other of said first and second fluid ports to form a flow path between one of said first and second fluid ports and the other of said first and second fluid ports port through the internal flow passage; and, whereby said stem when loaded with sample is inserted into said housing and unloaded by delivering fluid into one of said first and second fluid ports and through said internal flow passage so that sample fluid is moved to the other of said first and second fluid ports.

2. The injection apparatus of claim 1 wherein said internal flow passage contains porous material for holding sample until fluid passing through said internal flow passage extracts the sample.

3. The injection apparatus of claim 1 wherein said first opening is defined at said distal free end of said stem.

4. The injection apparatus of claim 1 wherein said proximal end of said stem is sealed and said second opening is defined in said side wall of said stem intermediate said distal free end of said stem and said holder and extends radially through said side wall.

5. The injection apparatus of claim 4 wherein at least one additional opening extends radially through said side wall near said second opening.

6. The injection apparatus of claim 1 wherein said first opening is defined at said distal free end of said stem, said proximal end of said stem is disposed within said holder, a proximal end opening to said internal flow passage is defined at said proximal end of said stem, and said holder defines a passageway between said proximal end opening and said second opening.

7. The injection apparatus of claim 6 wherein said passageway of said holder extends transversely through said holder and intersects said proximal end opening.

8. The injection apparatus of claim 1 wherein the side wall of said stem is cylindrical and extends linearly along a longitudinal axis and said injector flow passage is cylindrical and has an internal diameter where said stem is inserted at least as large as the external diameter of the side wall of said stem.

9. The injection apparatus of claim 8 wherein an annular seal is disposed along said injector flow passage providing a fluid seal between said housing and said side wall intermediate said first opening and said second opening when said injector stylus is inserted into said injector flow passage.

10. The injection apparatus of claim 1 wherein a first section of said injector flow passage extends linearly along a longitudinal axis between one of said first and second fluid ports and said insertion port and a second section of said injector flow passage transversely intersects said first section and communicates with the other of said first and second fluid ports.

11. The injection apparatus of claim 10 wherein said second section intersects said first section adjacent the furthest of said first and second opening from said distal free end of said stem when said injector stylus is inserted into said injector flow passage.

12. The injection apparatus of claim 1 wherein one of said first and second fluid ports is an injector inlet port for delivery of fluid into said injector flow passage and the other of said first and second fluid ports is an injector outlet port for withdrawal of sample fluid from said injector flow passage.

13. The injection apparatus of claim 1 wherein said securing means comprises an internal thread in said insertion port and a complementary external thread on said injector stylus to engage said internal thread and secure said injector stylus to said housing when inserted.

14. The injection apparatus of claim 1 wherein said first opening is defined at the distal free end of said stem and said proximal end of said stem is closed by said holder, and said second opening is defined in said side wall of said stem intermediate said distal free end of said stem and said holder and extends radially through said side wall.

15. The injection apparatus of claim 1 wherein said holder is diametrically larger than said proximal end of said stem and defines an external gripping surface for a user.

16. The injection apparatus of claim 15 wherein said injector stylus includes a recessed opening in an end of said holder for receiving a component having informational indicia.

17. An injection apparatus for use in delivering sample into a liquid chromatography system, comprising:

an injector stylus including a holder and an elongate tubular stem, said stem including a side wall with an internal diameter and an external diameter and having a proximal end mounted to said holder and extending longitudinally from said holder to a distal free end, said stylus defining an internal flow passage passing through said stem, the internal flow passage extending between a first opening and a second opening spaced from said first opening, said first and second openings each providing communication between said internal flow passage and the exterior of the stylus;

porous material within said internal passage for holding sample until fluid passing through said internal flow passage extracts the sample;

an injector having a housing defining a first fluid port, a second fluid port, an insertion port, and an injector flow passage providing communication between said first fluid port, said second fluid port, and said insertion port;

a first section of said injector flow passage extending linearly along a longitudinal axis between one of said first and second fluid ports and said insertion port and a second section of said injector flow passage intersecting said first section and communicating with the other of said first and second fluid ports;

securing means on said stylus and said injector for holding said stylus within said injector when said stylus is inserted through said insertion port into said injector flow passage;

wherein said injector stylus when inserted closes said insertion port with said first opening communicating with one of said first and second fluid ports and said second opening communicating with the other fluid port to form a flow path between one of said first and second fluid ports and the other of said first and second fluid ports through the internal flow passage; and, whereby said stem when loaded with sample is inserted into said housing and unloaded by delivering fluid into one of said first and second fluid ports and through said internal flow passage so that sample fluid is moved to the other of said first and second fluid ports.

18. The injection apparatus of claim 17 wherein said first opening is defined at said distal free end of said stem, said proximal end of said stem is sealed by said holder, and said second opening is defined in said side wall of said stem intermediate said first opening and said holder and extends radially through said side wall.

19. The injection apparatus of claim 17 wherein said first opening is defined at said distal free end of said stem, said proximal end of said stem is disposed within said holder, a proximal end opening to said internal flow passage is defined at said proximal end of said stem, and said holder defines a passageway between said proximal end opening and said second opening.

20. In a liquid chromatography system, a sample introduction device beatable along the flow passage of an injector housing, said device comprising:

an injector stylus including a holder and an elongate tubular stem;

said stem including a side wall with an internal diameter and an external diameter and having a proximal end mounted to said holder and extending longitudinally from said holder to a distal free end, said stylus defining an internal flow passage passing through said stem, the internal flow passage extending longitudinally between the distal free end and a stationary end wall fixed relative to the distal free end, the internal flow passage connecting between a first opening and a second opening spaced from said first opening, each of said openings providing communication between said internal flow passage and the exterior of the stylus;

porous material within said internal passage for holding sample until fluid passing through said internal flow passage extracts the sample;

whereby said stem when loaded with sample is inserted into said housing with respective openings communicating with upstream and downstream sections of the housing flow passage and unloaded by moving fluid through said internal flow passage of said stem.

21. The injection apparatus of claim 20 wherein said first opening is defined at said distal free end of said stem, said holder forms the end wall and seals said proximal end of said stem, and said second opening is defined in said side wall of said stem intermediate said first opening and said holder and extends radially through said side wall.

22. The injection apparatus of claim 20 wherein said first opening is defined at said distal free end of said stem, said proximal end of said stem is disposed within said holder, a proximal end opening to said internal flow passage is defined at said proximal end of said stem, and said holder forms the end wall and defines a passageway between said proximal end opening and said second opening.

23. The device of claim 20 wherein said stylus includes an external thread inward of the end opposite said stem, and further including an elongate cover with a longitudinal internal opening for receiving said stylus having a complementary internal thread to engage said external thread and releasably seal said stem within said cover when inserted.

* * * * *